United States Patent
Gustavsson

(10) Patent No.: US 8,858,229 B2
(45) Date of Patent: Oct. 14, 2014

(54) VOLUME EMITTER

(75) Inventor: Morgan Lars Ake Gustavsson, Newton, MA (US)

(73) Assignee: Morgan Gustavsson, Newport Beach, CA (US)

( * ) Notice: Subject to any disclaimer, the term of this patent is extended or adjusted under 35 U.S.C. 154(b) by 1286 days.

(21) Appl. No.: 12/199,488

(22) Filed: Aug. 27, 2008

(65) Prior Publication Data

US 2009/0059617 A1 Mar. 5, 2009

Related U.S. Application Data

(60) Provisional application No. 60/968,235, filed on Aug. 27, 2007, provisional application No. 60/977,181, filed on Oct. 3, 2007.

(51) Int. Cl.
| | |
|---|---|
| *A61N 5/06* | (2006.01) |
| *A61B 18/20* | (2006.01) |
| *A61B 18/18* | (2006.01) |
| *A61B 18/00* | (2006.01) |

(52) U.S. Cl.
CPC ....... *A61B 18/203* (2013.01); *A61B 2018/1807* (2013.01); *A61N 5/0616* (2013.01); *A61B 2018/00476* (2013.01); *A61B 2018/00452* (2013.01)
USPC .......................................... 433/90

(58) Field of Classification Search
USPC ....... 607/88–94; 606/2–19; 433/29; 362/572, 362/573, 263; 313/484, 110–114, 572, 568
See application file for complete search history.

(56) References Cited

U.S. PATENT DOCUMENTS

| | | |
|---|---|---|
| 4,370,175 A | 1/1983 | Levatter |
| 4,378,583 A | 3/1983 | Caprari |
| 4,498,183 A | 2/1985 | Levatter |
| 4,819,669 A | 4/1989 | Politzer |
| 4,940,922 A | 7/1990 | Schuda et al. |
| 4,983,889 A * | 1/1991 | Roberts .......................... 315/246 |
| 5,182,857 A | 2/1993 | Simon |

(Continued)

FOREIGN PATENT DOCUMENTS

| | | |
|---|---|---|
| DE | 102005057617 | 6/2007 |
| EP | 0 565 331 | 10/1993 |

(Continued)

OTHER PUBLICATIONS

Attwood et al., "Intense Pulsed Light for Aesthetic & Medical Application," PerkinElmer, White Paper Lighting Solutions, 4 pages (2004).

(Continued)

*Primary Examiner* — Yogesh Patel
(74) *Attorney, Agent, or Firm* — Knobbe, Martens, Olson & Bear, LLP.

(57) ABSTRACT

An apparatus for treating organic tissue includes: (i) a flash lamp defining a bore; (ii) a current source adapted for providing current to the flash lamp and operating at a current density adapted for forming a volume of optically transparent plasma within the bore, where the volume of optically transparent plasma is capable of emitting electromagnetic radiation and allowing the transmission of the electromagnetic radiation through the volume of optically transparent plasma; and (iii) a delivery system adapted for employing at least a portion of the electromagnetic radiation to treat the organic tissue.

11 Claims, 5 Drawing Sheets

(56) References Cited

U.S. PATENT DOCUMENTS

| | | | |
|---|---|---|---|
| 5,533,266 | A | 7/1996 | Kelman |
| 5,595,568 | A | 1/1997 | Anderson et al. |
| 5,606,798 | A | 3/1997 | Kelman |
| 5,735,844 | A | 4/1998 | Anderson et al. |
| 6,217,572 | B1 | 4/2001 | Tobinick |
| 6,533,775 | B1 | 3/2003 | Rizoiu |
| 6,699,236 | B1 | 3/2004 | Godfried et al. |
| 6,888,319 | B2 | 5/2005 | Inochkin et al. |
| 6,982,046 | B2 * | 1/2006 | Srivastava et al. ..... 252/301.4 R |
| 7,102,141 | B2 | 9/2006 | Hwang et al. |
| 7,108,689 | B2 * | 9/2006 | Eckhouse et al. ................. 606/9 |
| 7,274,155 | B2 | 9/2007 | Inochkin et al. |
| 2003/0057836 | A1 * | 3/2003 | Koenigsberg et al. ........ 313/634 |
| 2004/0254619 | A1 * | 12/2004 | Feuermann et al. ............ 607/88 |
| 2005/0147137 | A1 | 7/2005 | Slatkine |
| 2006/0269580 | A1 * | 11/2006 | Cole et al. ..................... 424/401 |
| 2007/0267974 | A1 * | 11/2007 | Fuse et al. ..................... 313/606 |
| 2008/0215124 | A1 * | 9/2008 | Wagenaar Cacciola et al. ................. 607/90 |
| 2010/0213867 | A1 * | 8/2010 | Kaening et al. ............... 315/291 |

FOREIGN PATENT DOCUMENTS

| | | |
|---|---|---|
| WO | WO 93/05920 | 4/1993 |
| WO | WO 03/003903 | 1/2003 |
| WO | WO 2007/033687 | 3/2007 |

OTHER PUBLICATIONS

Linford, G., "Time-resolved Xenon Flash-lamp Opacity Measurements," *Applied Optics*, 33(36):8333-8345 (1994).

Noble, L., "Optical Pumps for Lasers. vol. I," ILC Technology Inc., Sunnyvale, CA (1973).

"The Lamp Book, The Heraeus Noblelight Technical Reference Book for Arc and Flash Lamps," Heraeus Noblelight Limited (publication date unknown, last accessed at www.heraeus-noblelight.com Aug. 2008).

"High Performance Flash and Arc Lamps," PerkinElmer Optoelectonics Product Brochure (publication date unknown, last accessed at www.perkinelmer.com/opto Aug. 2008).

"A Guide to Flashlamps for Pulsed Solid State Lasers," Technical Bulletin 2, ILC Technology, 16 pages (1983).

"An Overview of Flashlamps and CW Arc Lamps, " Technical Bulletin 3, ILC Technology, 46 pages (1986).

"Laserlampen Katalog," Laser Components (last accessed at http://www.lasercomponents.com/de/fileadmin/user_upload/home/Datasheets/amglo/laserlampen_katalog-d.pdf Aug. 2008) 5 pages (2005).

"Laser Lamps," Sintec Optronics Product Broshure (last accessed at http://www.sintecoptronics.com/lamp.htm Aug. 2008) 5 pages (2006).

"Super-Quiet Xenon Flash Lamp Series," Hamamatsu Product Catalouge (last accessed at http://sales.hamamatsu.com/assets/pdf/catsandguides/Xe-F_TLSX1048E02.pdf Aug. 2008) 15 pages (2006).

International Search Report for International Application No. PCT/US2008/074471, Date of Mailing Jan. 15, 2009 (5 pages).

Wekhof, A., "Disinfection with Flash Lamps". PDA Journal of Pharmaceutical Science and Technology, 54(3), pp. 264-276, May/Jun. 2000.

Emmet, J.L. et al. "Direct measurement of Xenon Flashtube Opacity". Submitted for publication in the Journal of Applied Physics, 21 pages, Jan. 1, 1964.

"An Introduction to Flashlamps". Technical Bulletin 1, 2 and 3 by ILC Technology, Inc., Sunnyvale, CA, 1989.

\* cited by examiner

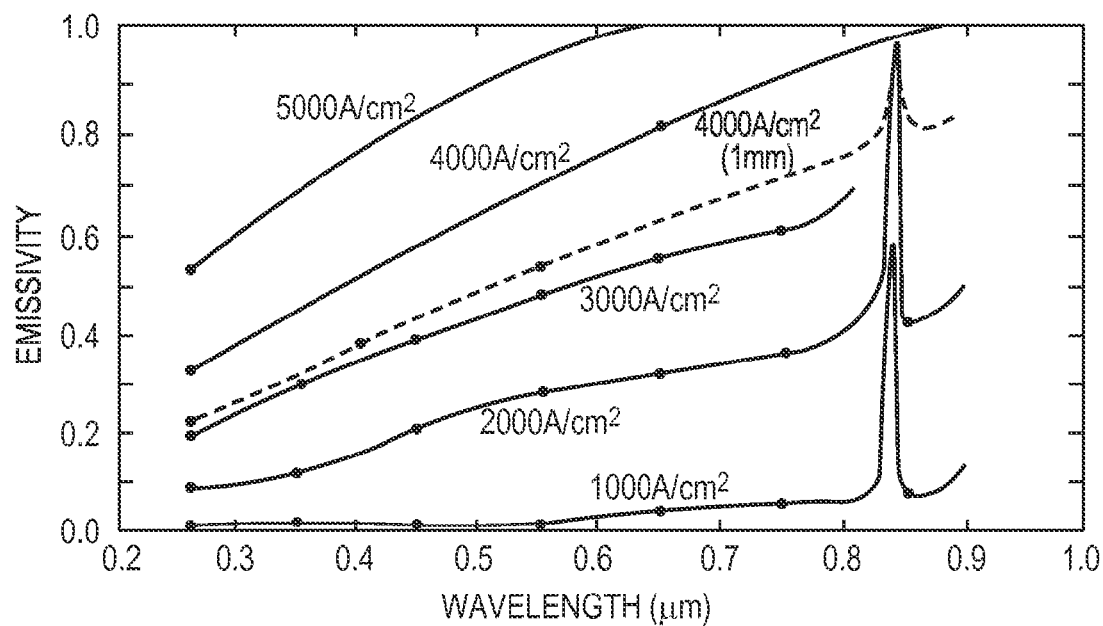
FIG. 1 - Prior Art
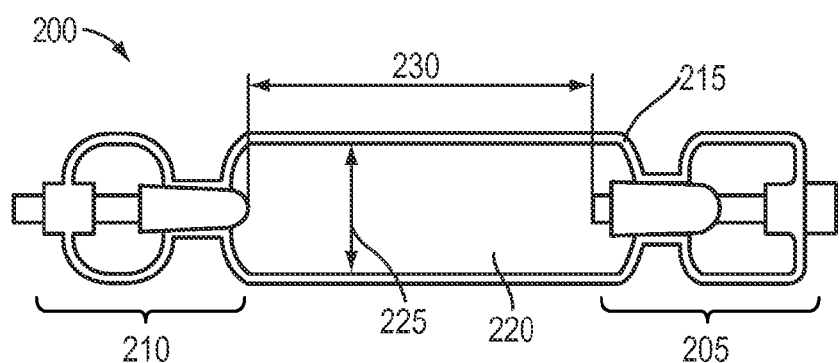
FIG. 2

VOLUME EMITTER

CROSS-REFERENCE TO RELATED APPLICATIONS

This application claims benefit of priority to Application No. 60/968,235, filed Aug. 27, 2007 and entitled "Volume Emitter" by Gustavsson and to Application No. 60/977,181, filed Oct. 3, 2007 and entitled "Volume Emitter" by Gustavsson, the disclosures of which are incorporated herein by reference in their entireties.

FIELD OF THE INVENTION

In general, the invention relates to apparatuses and methods for treating organic tissue with a flash lamp. In particular, the invention relates to apparatuses and methods for treating organic tissue with electromagnetic radiation from a flash lamp operating at a current density adapted for forming a volume of optically transparent plasma within the bore.

BACKGROUND OF THE INVENTION

Flash lamps have a wide range of medical and cosmetic, as well as industrial, applications. Flash lamps in intense pulse light (IPL), fluorescent pulsed light (FPL), fluorescent light, or laser light sources for medical and cosmetic application function predominantly through plasma surface (e.g., blackbody) emission of electromagnetic radiation. One reason for the predominance of plasma surface emission is the empirical observation and working hypothesis that the emissivity and electro-optical efficiency of a flash lamp increases with current density, which points to the conclusion that high current density is needed to meet the practical need for emission of sufficient electromagnetic radiation. Another reason for the predominance of plasma surface emission is the great success of such flash lamps in the field of laser pumps, where surface emission is desirable and beneficial, which has resulted in successful laser technology being directly carried over for medical and cosmetic use.

In flash lamp design, the working hypothesis that higher efficiency results from higher current density operation (e.g., current density sufficient to support substantially blue-shifted or at least some blackbody radiation), lead naturally to the working hypothesis that higher efficiency can also be achieved through use a flash lamp having a smaller bore. Because the blackbody emission occurs from the plasma surface, and because the plasma (e.g., the volume of gas plasma inside the lamp) is opaque to the emission, flash lamp bore size is generally minimized to maximize the surface area to volume ratio and to minimize the loss of electromagnetic radiation emitted from within the volume of gas plasma inside the lamp (e.g., electromagnetic radiation that is not transmitted through the opaque plasma).

FIG. 1 shows calculated spectral emissivity curves for a 5 mm bore diameter 450 Torr Xenon lamp at various current densities. FIG. 1 also shows a calculated spectral emissivity curve for a 3 mm bore diameter 450 Torr Xenon lamp for comparison. Therefore, FIG. 1 illustrates the hypothesis that (i) emissivity and electro-optical efficiency should increase with increasing current density and that (ii) a small bore size is generally desirable.

In practice, the fact that at least some area of plasma surface is needed for emission and the fact that the surface emitting plasma is opaque has also kept the arc-length to bore ratio of traditional flash lamps relatively large (e.g., greater than about 12-9) and bore sizes relatively small (e.g., less than about 4-7 mm). Such traditional designs employ relatively high current densities (e.g., greater than about 5,000 Amps/cm$^2$) to drive the flash lamp to produce peak wavelengths suitable, for example, for pumping Nd:YAG lasers. Even with relatively high current density operation, practioners and designers of flash lamp-based devices still seek to increase the output of their devices. Various lamp configurations have traditionally been attempted to improve fluence. These configurations include: IPLs with lamps next to each other, IPLs with lamps on top of each other, and U-shaped lamps. Each of these lamp configurations is characterized by a relatively small bore size.

Such small bore, high current density designs have continued to be used and developed because they are well-suited for many commercially significant applications. One reason that small bore, high current density designs have been successful and are pervasive in the flash lamp market is that they produce large amounts of broad band and blue-green light. In fact, high current densities result in high temperatures, which can cause blue shift in the emission spectrum and which can cause the flash lamp to function as a black body emitter (e.g., through surface emission), which was deemed to be largely desirable, useful, and efficient for laser pumping. These empirical observations have been carried over to IPL and FPL devices for medical and cosmetic application, resulting in small bore, high current density flash lamps dominating IPL and FPL devices for medical and cosmetic fields.

Although it is known that a flash lamp can provide at least some electromagnetic radiation under low current densities (e.g., as shown in FIG. 1), such low current density operation has not been previously demonstrated for treating organic tissue. Generally, it was believed low current density operation of a flash lamp did not provide sufficient electromagnetic radiation to effect a treatment.

For example, not only did naked conventional flash lamps (e.g., less than about 4-7 mm bore diameter) emit little electromagnetic radiation, but the necessity for filters to remove harmful and non-therapeutic bands of electromagnetic radiation (e.g., UV light), further reduced the output of flash lamps operating at low current densities to the point where the lamps were too inefficient to effect treatment or were simply incapable of affecting any treatment at all. Furthermore, the prediction of flash lamp output based on structural design and operating parameters is notoriously unreliable. Therefore, the design and operation of flash lamps continues to be dominated by the empirical observations and practical experience that small-bore, high current density flash lamps are preferable and desirable.

BRIEF SUMMARY OF THE INVENTION

The invention, in various aspects and embodiments, features a flash lamp apparatus having improved electro-optical efficiency. For example, the apparatus can be a light source such as an IPL, FPL, fluorescent light, or laser light source. An apparatus employing a flash lamp according to the invention (e.g., having a 13 mm bore operated with a sub 1000 Amps/cm$^2$ current density) can have a electro-optical efficacy of about 40%, which is greater than twice the 20% electro-optical efficacy of a conventional flash lamp apparatus (e.g., having a 6 mm bore lamp at about 5000 Amps/cm$^2$). The flash lamp can have a relatively large bore (e.g., greater than about 7 mm). More particularly, the flash lamp can have a relatively small arc-length to bore ratio (or, relatively large bore to arc-length ratio).

In certain embodiments, the invention features a flash lamp capable of being operated at a current density adapted for forming a volume of optically transparent plasma within the bore of the flash lamp, where the volume of optically transparent plasma is capable of emitting electromagnetic radiation and allowing the transmission of the electromagnetic radiation through the volume of optically transparent plasma. The electromagnetic radiation produced through this "volume emission" can be delivered to organic tissue, to treat the organic tissue.

Therapeutic treatments include treatments for disease (e.g., any medical condition caused by a pathogen, genetics, injury, inflammation, and the like) and cosmetic treatments (e.g., any condition desired by a patient for cosmetic reasons, even where not medically indicated). In various embodiments, the organic tissue is skin or structures or conditions therein. Organic tissue can also include any one or more of hair follicles, fatty tissue, vasculature, glands, ducts, and vessels. Conditions and treatments can include hair removal, reduction, or regrowth (each either temporary or permanent), vascular lesions, pigmented lesions, bruising, unwanted fat, water retention, tattoo removal, pores, wrinkles and fine lines, dyschromia (e.g., skin discoloration), infection (e.g., bacterial, viral, eukaryotic, or fungal), inflammation, infestation, pain, acne, cellulite, psoriasis, and vitiligo. Conditions can also include arthritis, myositis, tendinitis, periostitis, gingivitis, fibromyalgitis, pain.

The invention, in various aspects and embodiments, includes numerous potential advantages. For example, the invention includes a flash lamp apparatus with improved (e.g., doubled) electro-optical efficiency compared to prior art flash lamps. Because the flash lamp apparatus operates with higher efficiency, the demands on the electrical circuitry (e.g., capacitor bank, capacitor bank charger, insulated gate bipolar transistor and power diode, discharge unit) can be reduced (e.g., an apparatus may require half the electricity, and half the corresponding electrical equipotent of a prior art flash lamp apparatuses). Because the flash lamp apparatus operates with higher efficiency, heat production and thus the demands for cooling (e.g., water pump, hear exchanger, radiator, fan) can be reduced (e.g., an apparatus may require half the cooling, or no active cooling at all). Because the flash lamp apparatus operates with higher efficiency, the flash lamp apparatus can produce a larger (e.g., double) spot size or rep rate using the same voltage and current as a prior art flash lamp apparatuses. In turn, the flash lamp apparatus can increase the speed of treatment (e.g., half), which decreases a subject's discomfort, decreases treatment cost, and increases a practitioner's potential profit margin. Furthermore, because the flash lamp apparatus operates with higher efficiency, the flash lamp can operate at a cooler temperature, which increases (e.g., double or ten times) the operating lifetime of the flash lamp. Increased flash lamp lifetime also decreases operating cost and apparatus down time, increases a practitioner's potential profit margin.

In one aspect, the invention features an apparatus for treating organic tissue. The apparatus includes a flash lamp defining a bore. The apparatus also includes a current source delivering current to the flash lamp and operating at a current density that facilitates the formation of a volume of optically transparent plasma within the bore, where the volume of optically transparent plasma is capable of emitting electromagnetic radiation and allowing the transmission of the electromagnetic radiation through the volume of optically transparent plasma. Additionally, the apparatus includes a delivery system employing at least a portion of the electromagnetic radiation to treat the organic tissue.

In another aspect, the invention features a method for treating organic tissue. The method includes providing current to a flash lamp at a current density adapted for forming a volume of optically transparent plasma within a bore of the flash lamp, where the volume of optically transparent plasma is capable of emitting electromagnetic radiation and allowing the transmission of the electromagnetic radiation through the volume of optically transparent plasma. The method also includes employing at least a portion of the electromagnetic radiation to treat the organic tissue.

In still another aspect, the invention features a method for removing hair from organic tissue. The method includes providing current to a flash lamp at a current density adapted for forming a volume of optically transparent plasma within a bore of the flash lamp, where the volume of optically transparent plasma is capable of emitting electromagnetic radiation and allowing the transmission of the electromagnetic radiation through the volume of optically transparent plasma. The method also includes employing at least a portion of the electromagnetic radiation to remove hair from the organic tissue.

In yet another aspect, the invention features a method for providing electromagnetic radiation capable of treating organic tissue. The method includes providing current to a flash lamp at a current density adapted for forming a volume of optically transparent plasma within a bore of the flash lamp. The method also includes collecting a first portion of electromagnetic radiation emitted from the volume of optically transparent plasma. The method also includes allowing transmission of a second portion of electromagnetic radiation through the volume of optically transparent plasma. The method also includes collecting the second portion of the electromagnetic radiation transmitted through the optically transparent plasma, to increase the electromagnetic radiation capable of treating organic tissue.

In still yet another aspect, the invention features a method including delivering current having a current density to a flash lamp. The method also includes forming a volume of optically transparent plasma within a bore of the flash lamp, the volume of optically transparent plasma emitting electromagnetic radiation. The method also includes delivering at least a portion of the electromagnetic radiation to organic tissue.

In other embodiments, any of the aspects above, or any apparatus, method, or kit described herein, can include one or more of the following features.

In various embodiments, the apparatus includes a reflector disposed relative to the flash lamp for reflecting a second portion of the electromagnetic radiation back through the optically transparent plasma to the delivery system.

In some embodiments, the portion of the electromagnetic radiation comprises electromagnetic radiation emitted from throughout the volume of optically transparent plasma and transmitted from within the volume of optically transparent plasma and through the volume of optically transparent plasma.

In certain embodiments, the delivery system comprises a waveguide for receiving electromagnetic radiation from the flash lamp and delivering the portion of the electromagnetic radiation to the organic tissue.

In various embodiments, the delivery system comprises a body for receiving electromagnetic radiation from the flash lamp and transforming the electromagnetic radiation into radiation having a second wavelength to the organic tissue.

In some embodiments, the bore diameter is greater than about 7 mm. In one embodiment, the bore diameter is greater than about 9 mm. In one embodiment, the bore diameter is greater than about 11 mm.

In certain embodiments, the flash lamp comprises a cathode and an anode separated by an arc path length, and an arc path length to bore diameter ratio of less than about 1. In one embodiment, the flash lamp comprises a cathode and an anode separated by an arc path length, and an arc path length to bore diameter ratio of less than about 6.

In one embodiment, the flash lamp comprises a cathode and an anode separated by an arc path length, and an arc path length to bore diameter ratio of less than about 12.

In various embodiments, the current density is below about 1,000 Å/cm$^2$. In one embodiment, the current density is below about 2,000 Å/cm$^2$. In one embodiment, the current density is below about 3,000 Å/cm$^2$.

In some embodiments, the optically transparent plasma has a transmission coefficient of greater than about 0.35 for a 1 cm path length at a wavelength of about 5,500 Å.

In certain embodiments, the method includes reflecting a second portion of the electromagnetic radiation back through the optically transparent plasma to the delivery system, to increase the portion of the emitted electromagnetic radiation to treat the organic tissue.

In various embodiments, employing at least a portion of the electromagnetic radiation to treat the organic tissue comprises delivering the portion of the electromagnetic radiation to the organic tissue.

In some embodiments, employing at least a portion of the electromagnetic radiation to treat the organic tissue includes (i) transforming the portion of the electromagnetic radiation into radiation having a second wavelength and (ii) delivering the radiation having the second wavelength to the organic tissue.

In certain embodiments, the flash lamp has an explosion energy and the flash lamp is provided current at less than about 15% of the explosion energy. In one embodiment, the flash lamp has an explosion energy and the flash lamp is provided current at less than about 7.5% of the explosion energy.

In various embodiments, the flash lamp has an electro-optical efficiency of greater than about 20%. In one embodiment, the flash lamp has an electro-optical efficiency of greater than about 30%. In one embodiment, the flash lamp has an electro-optical efficiency of greater than about 40%.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 1 shows calculated spectral emissivity curves for a 5 mm bore diameter 450 Torr Xenon lamp at various current densities.

FIG. 2 shows a flash lamp including a cathode, an anode, and an envelope defining a cavity.

DETAILED DESCRIPTION OF THE INVENTION

Figure 3:
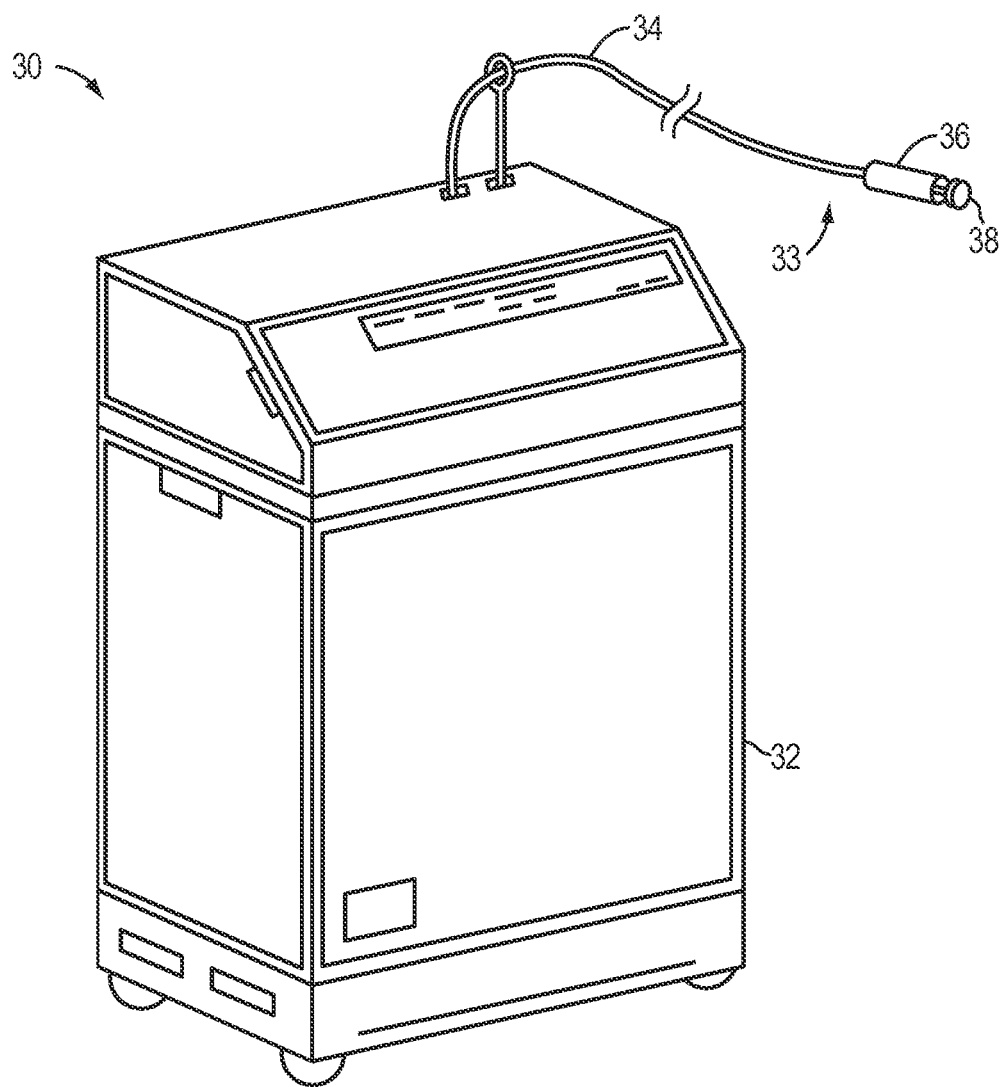
FIG. 3 shows a system for employing a flash lamp apparatus having improved electro-optical efficiency.

FIG. 2 shows a flash lamp 200 including a cathode electrode 205, an anode electrode 210, and an envelope 215 defining a cavity 220. The envelope 215 can be any material used in the manufacture of flash lamps (e.g., a quartz envelope such as titanium-doped quartz). The cavity can be filled with any gas used in the manufacture of flash lamps (e.g., Xenon, Krypton, or combination thereof). The flash lamp has a bore dimension 225, which can be measured, for example, as the internal diameter of the cavity. The flash lamp has an arc length dimension 230, which can be measured, for example as the distance between portions of the cathode and anode or, more generally, between two electrodes. The flash lamp can include various components used in the manufacture of flash lamps (e.g., o-ring seals and electrical contacts). The envelope material, fill pressure, bore diameter, and arc length can be selected to achieve desired operating and emission parameters (e.g., operating current density, output fluence, output wavelength).

In operation, the flash lamp can be driven at a current density adapted for forming a volume of optically transparent (e.g., at least partially, substantially, or essentially transparent) plasma within the bore, wherein the volume of optically transparent plasma is capable of emitting electromagnetic radiation and allowing the transmission of the electromagnetic radiation through the volume of optically transparent plasma. The electromagnetic radiation can include electromagnetic radiation emitted from throughout the volume of optically transparent plasma and transmitted from within the volume of optically transparent plasma and through the volume of optically transparent plasma.

In various embodiments, the flash lamp is driven by a current density of not more than about 4,500, 4,000, 3,500, 3,000, 2,500, 1,500, 1,000, or 500 Amps/cm$^2$. In one embodiment, impedance can be balanced with a voltage to produce the desired current density. Importantly, the flash lamp can emit sufficient electromagnetic radiation to effect treatment of organic tissue.

In various embodiments, the flash lamp is characterized by a bore of a diameter of at least about 7, 8, 9, 10, 1, or 12 mm. In one embodiment, the bore diameter is greater than about 12 mm.

In various embodiments, the flash lamp is characterized by an arc-length to bore ratio of not more than about 9.0, 8.5, 8.0, 7.5, 7.0, 6.5, 6.0, 5.5, 5.0, 4.5, 4.0, 3.5, 3.0, 2.5, 2.0, 1.5, or 1.0.

In various embodiments, the flash lamp has an explosion energy, and the flash lamp is provided current at less than about 15% of the explosion energy. In one embodiment, the flash lamp is provided current at less than about 7.5% of the explosion energy. Operating well below a lamp's explosion energy can lead to a longer operating lifetime. The flash lamp can operate effectively at lower currents than many prior art flash lamps (e.g., for medical or cosmetic treatments) due to its higher electro-optical efficiency.

In various embodiments, the flash lamp (e.g., any flash lamp, or system including a flash lamp, according to the invention) can have an electro-optical efficiency of greater than about 20%. In one embodiment, the electro-optical efficiency of greater than about 30%. In one embodiment, the electro-optical efficiency of greater than about 40%.

FIG. 3 shows a system 30 for employing a flash lamp having improved electro-optical efficiency, such as flash lamp 200. The system 30 can be used to non-invasively deliver radiation to a target region, and can be an IPL, FPL, fluorescent light, or laser system. For example, the radiation can be delivered through an external surface of skin over the target region. The system 30 includes an energy source 32 and a delivery system 33. In one embodiment, radiation provided by the energy source 32 is directed via the delivery system 33 to a target region. In the illustrated embodiment, the delivery system 33 includes a fiber 34 having a circular cross-section and a handpiece 36. Radiation can be delivered by the fiber 34 to the handpiece 36, which can include an optical system (e.g., an optic or system of optics) to direct the radiation to the target region. A user can hold or manipulate the handpiece 36 to irradiate the target region. The delivery system 33 can be positioned in contact with a skin surface, can be positioned adjacent a skin surface, can be positioned proximate a skin surface, can be positioned spaced from a skin surface, or a combination of the aforementioned. In the embodiment shown, the delivery system 33 includes a spacer 38 to space the delivery system 33 from the skin surface. In one embodiment, the spacer 38 can be a distance gauge, which can aid a practitioner with placement of the delivery system 33.

In various embodiments, delivery system 33, or any other delivery system can be adapted for employing at least a portion of the electromagnetic radiation to treat the organic tissue. In one embodiment, the delivery system includes a waveguide for receiving electromagnetic radiation from the flash lamp and delivering the portion of the electromagnetic radiation to the organic tissue. In one embodiment, the delivery system comprises a body for receiving electromagnetic radiation from the flash lamp and transforming the electromagnetic radiation into radiation having a second wavelength to the organic tissue (e.g., a fluorescent optic or laser dye).

In various embodiments, the system 30 or any other system described herein can include a capacitor bank for driving the flash lamp at a current density of not more than about 4,500, 4,000, 3,500, 3,000, 2,500, 1,500, 1,000, or 500 Amps/cm$^2$.

In various embodiments, the system 30 or any other system described herein can emit electromagnetic radiation characterized by an energy density between about 0.1 J/cm$^2$ and about 500 J/cm$^2$. In various embodiments, the electromagnetic radiation delivered to the organic tissue can be characterized by an energy density between about 0.1 J/cm$^2$ and about 40 J/cm$^2$, or about 1 J/cm$^2$ and about 18 J/cm$^2$. In certain embodiments, the energy density can be about 0.1, 0.5 1, 5, 10, 50, 100, 150, 200, 250, 300, 350, 400, or 450 J/cm$^2$, or any value therebetween.

The energy density can be selected to be sufficient to treat the organic tissue. For example, for a vascular lesion, the energy density can be between about 10 J/cm$^2$ and about 100 J/cm$^2$. However, the energy density can vary depending upon the wavelength of the electromagnetic radiation and the characteristics of the lesion.

In various embodiments, the system 30 or any other system described herein can emit electromagnetic radiation characterized by a pulse width between about 10 µs and about 2 s. In one embodiment, the electromagnetic radiation is characterized by a pulse width between about 1 ms and about 120 ms. A pulse width can be about 10, 20, 30, 40, or 50 ms. A pulse width can be selected based upon the type of treatment and/or the type of skin being treated. Pulses can be single or repetitive, and can have a frequency between about 0.1 Hz and about 1000 Hz or between about 0.1 Hz and about 100 Hz or in bursts of pulses coming in btw 0.1 Hz and 10 Hz.

In various embodiments, the system 30 or any other system described herein can emit electromagnetic radiation characterized by a spot size between about 0.1 cm$^2$ and about 40 cm$^2$. In one embodiment, the spot size is between about 1 cm$^2$ and about 18 cm$^2$. A spot size can be up to about 1, 2, 3, 4, or 5 mm in diameter. In various embodiments, the optic can produce a spot size of about 2 mm or greater in diameter. A waveguide or optic (e.g., included in the delivery system) can define a spot size by the diameter and shape of the waveguide or optic. In laser systems, the spot is generally round. In IPL systems, the spot is generally square.

In various embodiments, the system 30 or any other system described herein can include a filter to prevent harmful or otherwise undesirable wavelengths of electromagnetic radiation emitted from the flash lamp from reaching the organic tissue.

In various embodiments, flash lamp apparatuses having improved electro-optical efficiency can include systems with a detachable handpiece and compact, handheld devices.

Figure 4:
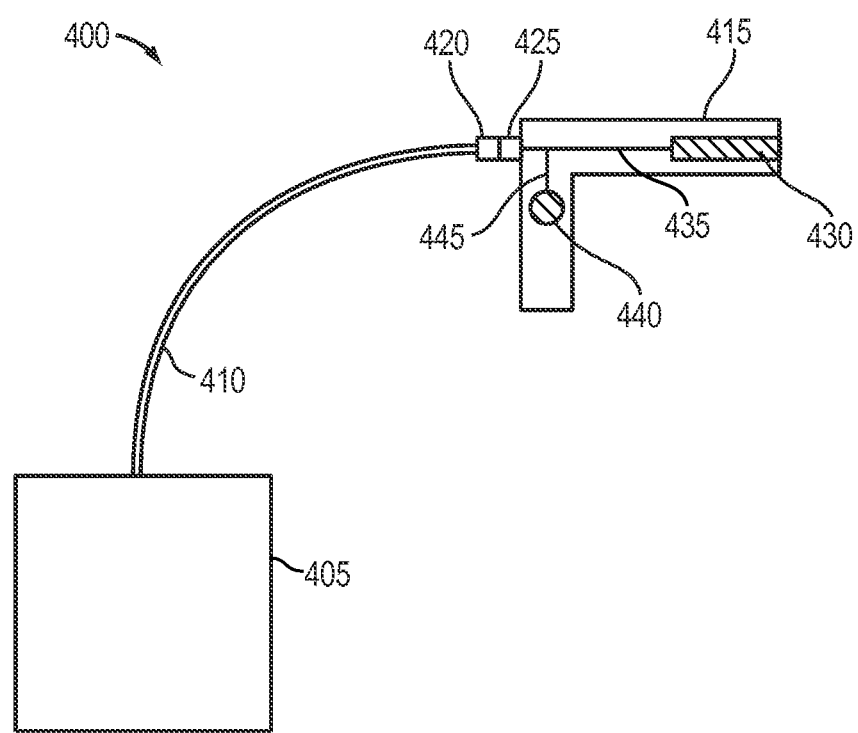
FIG. 4 shows an apparatus, which can incorporate a flash lamp apparatus having improved electro-optical efficiency, for treating organic tissue using electromagnetic radiation.

FIG. 4 shows an apparatus 400, which can incorporate a flash lamp (e.g., flash lamp 200) having improved electro-optical efficiency for treating organic tissue using electromagnetic radiation. The apparatus 400 includes a base unit 405, an umbilicus 410, and a handpiece 415. The base unit 405 can include a power source, computer, electronics, cooling elements, and/or other components. The umbilicus 410 connects the base unit 405 to the handpiece 415. The umbilicus 410 can include one or more conduits for communicating power, signal, fluid, and/or gas from a first end to a second end, e.g. between the base unit 405 and the handpiece 415. In various embodiments the second end of the umbilicus 410 is directly, or indirectly, associated with the handpiece 415. In one embodiment, the second end of the umbilicus 410 can be associated with a first 420 connector. In one embodiment, the handpiece 415 can be associated with a second 425 connector that is detachably connectable to the first 420 connector. The handpiece 415 can be in at least one of efferent and afferent signal communication with the base unit 405.

The handpiece 415 also includes a source of electromagnetic radiation 430 (e.g., that incorporates a flash lamp according to the technology having improved electro-optical efficiency) adjacent a second portion of the handpiece and in communication with the second 425 connector through a first 435 conduit, for receiving energy from the second 425 connector to drive the source of electromagnetic radiation 430. The handpiece 415 can also include a controller 440 for controlling the source of electromagnetic radiation. The controller 440 is in communication with the source of electromagnetic radiation 430 through a second 445 conduit. In some embodiments, the controller 440 is in communication with the umbilicus 410 through a second 445 conduit. The handpiece 415 can include filters and optics for delivering the electromagnetic radiation to organic tissue. Power can also be used to drive and/or control the source of electromagnetic radiation. A signal can be used to control the output of the source of electromagnetic radiation (e.g., set, maintain, or control parameters of emitted radiation). Cooling elements can include a water pump, a heat exchanger, a thermoelectric cooler, and/or a fan. The controller 440 can send and/or receive the signal. In various embodiments, the controller 440, or a computer, electronics, or other components in the base unit 405 can control the pulse power, shape, length, or repetition rate. In one embodiment, the output of the source of electromagnetic radiation is controlled by controlling the power delivered to the source of electromagnetic radiation.

The fluid and/or gas can be used to cool the source of electromagnetic radiation and/or a transparent or translucent member contacting the skin during treatment.

In certain embodiments, the apparatus includes a signal source for providing a signal for regulating the source of electromagnetic radiation. The apparatus can include a controller associated with the handpiece and in communication with the signal source and the source of electromagnetic radiation, for regulating the source of electromagnetic radiation. The umbilicus can be adapted to facilitate communication between the signal source and the source of electromagnetic radiation. The signal source can be adapted for transmitting and/or receiving a wireless signal and the controller can be adapted for transmitting and/or receiving the wireless signal for regulating the source of electromagnetic radiation. The apparatus can include a controller adapted for regulating at least one property of the energy received by the source of electromagnetic radiation, for regulating the source of electromagnetic radiation.

In various embodiments, the source of electromagnetic radiation incorporates a flash lamp apparatus having improved electro-optical efficiency. However, the source of electromagnetic radiation can also include a laser, a coherent light source, or an incoherent light source. FPL technologies can utilize laser-dye impregnated polymer filters to convert unwanted energy from a xenon flash lamp into wavelengths that enhance the effectiveness of the intended applications. FPL technologies can be more energy efficient and can generate significantly less heat than comparative IPL systems. A FPL system can be adapted to operate as a multi-purpose treatment system by changing filters or handpieces to perform different procedures. For example, separate handpieces allow a practioner to perform tattoo removal and other vascular treatments.

In various embodiments, the apparatus for treating organic tissue using electromagnetic radiation can include a cooling system to modulate the temperature in a region of organic tissue and/or minimize unwanted thermal injury to untargeted organic tissue. For example, the cooling system can cool the organic tissue before, during, or after delivery of radiation, or a combination of the aforementioned. Cooling can include contact conduction cooling, evaporative spray cooling, convective air flow cooling, or a combination of the aforementioned. In various embodiments, the flash lamp requires less (e.g., about half) cooling than a conventional flash lamp. In one embodiment, the flash lamp produces about half of the heat of a conventional flash lamp or conventional IPL or FPL device.

In various embodiments, the flash lamp apparatus has a greater (e.g., about twice) electro-optical efficacy than a conventional flash lamp apparatus, or conventional IPL or FPL device. In one embodiment, the flash lamp apparatus can be twice as powerful or have double the spot size of a conventional flash lamp or conventional IPL or FPL device using the same input power (e.g., AC wall outlet or capacitor).

Due the greater electro-optical efficacy, the apparatus employing the flash lamp can have at least one of about half the charging capacity, about half the capacitor bank, about half the capacitor switching, or about half the capacitor safety-dumping capability of a conventional laser or conventional IPL or FPL device.

Due the greater electro-optical efficacy, the flash lamp can effectively operate at lower current density, lower temperature, or both. Accordingly, the flash lamp can have a lifetime of at least about 0.5, 1, 2, 3, 4, 5, 6, 7, 8, 9, 10, or more million pulses or pulse-trains. In one embodiment, the flash lamp has a lifetime of about 0.5, 1, 2, 3, 4, 5, 6, 7, 8, 9, 10, or more times greater than a conventional flash lamp.

Figure 5:
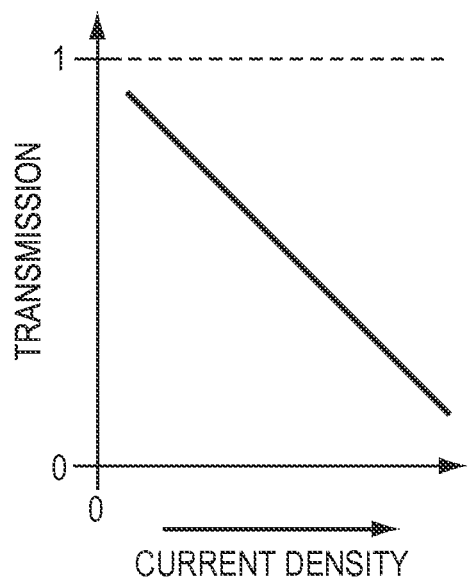
FIG. 5 shows the relationship between operating current density and transmission coefficient in a flash lamp.

FIG. 5 shows the relationship between operating current density and transmission coefficient in a flash lamp. In general, the transparency of plasma in a flash lamp decreases as operating current density increases. For example, a Xenon flash lamp filled at 300 Torr and having an approximately 165 mm arc length and a 12 mm bore diameter has an essentially transparent plasma when operated at about 1,000 Amps/cm$^2$, but an essentially opaque plasma when operated at about above about 4,000 Amps/cm$^2$ (e.g., transmission coefficient of about 1 versus about 0 at 5,500 Å for a 1 cm path length).

In various embodiments, the optically transparent plasma has a transmission coefficient of greater than about 0.35 for a 1 cm path length at a wavelength of about 5,500 Å. The optically transparent plasma can have a transmission coefficient of about 0.40, 0.45, 0.50, 0.55, 0.60, 0.65, 0.70, 0.75, 0.80, 0.85, 0.90, 0.95, or 1.0 for a 1 cm path length at a wavelength of about 5,500 Å.

Optical transparency can be related to the bore diameter. For example, a larger bore diameter can require a higher transmission coefficient (e.g., to minimize the percent of emitted electromagnetic radiation loss over a larger optical path length). However, this consideration may be tempered by the fact that a larger bore diameter also corresponds to more emission of electromagnetic radiation (e.g., a larger emitting volume of plasma).

In contrast, in an opaque plasma (i.e., conventional flash lamp operated at a high current density) the emitted electromagnetic radiation can be re-absorbed by the plasma, which heats the plasma and thus increases opaqueness. This results both increased heat and a blue shifted (i.e., shorter wave length) spectrum. Shorter wave lengths (e.g., UV) can be absorbed by the organic tissue (e.g., skin or epidermis) and cause side effects such as burn injuries, hypo pigmentation, and post inflammatory hyperpigmentation.

Figure 6:
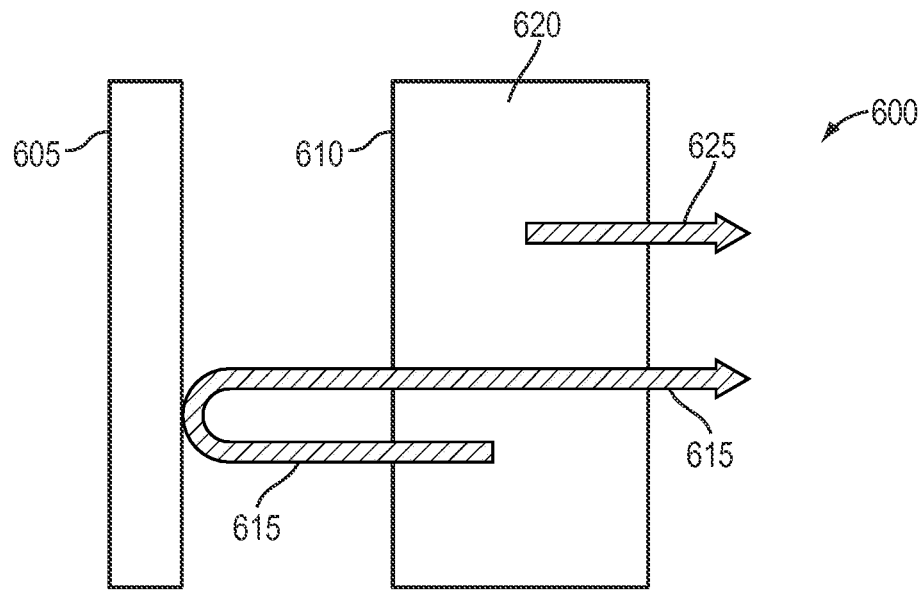
FIG. 6 shows an apparatus having a reflector disposed relative to a flash lamp for reflecting a second portion of the electromagnetic radiation back through the optically transparent plasma to the delivery system.

FIG. 6 shows an apparatus 600 having a reflector 605 disposed relative to a flash lamp 610, for reflecting a second portion 615 of the electromagnetic radiation back through the optically transparent plasma 620 to the delivery system (e.g., a delivery system as shown in FIG. 4 or 5). In operation, the flash lamp 610 is operated at a current density adapted for forming a volume of optically transparent plasma 620 within the bore. The volume of optically transparent plasma 620 is capable of emitting electromagnetic radiation and allowing the transmission of the electromagnetic radiation through the volume of optically transparent plasma 620.

The portion 625 of the electromagnetic radiation, emitted from within the volume of the transparent plasma 620, can be directed to the delivery system. Note that electromagnetic radiation is emitted from throughout the volume of the transparent plasma 620, and can travel though the volume of the transparent plasma 620 (e.g., the volume of the transparent plasma 620 is at least partially optically transparent).

The second portion 615 of the electromagnetic radiation travels through the volume of the transparent plasma 620 away from the delivery system and toward the reflector 605. The reflector 605 then reflects the second portion 615 back through the optically transparent plasma 620 to the delivery system. Accordingly, the efficiency of an apparatus employing the reflector 605 disposed relative to the flash lamp 610 is increased because a greater portion of the emitted electromagnetic radiation is directed to the delivery system.

Figure 7:
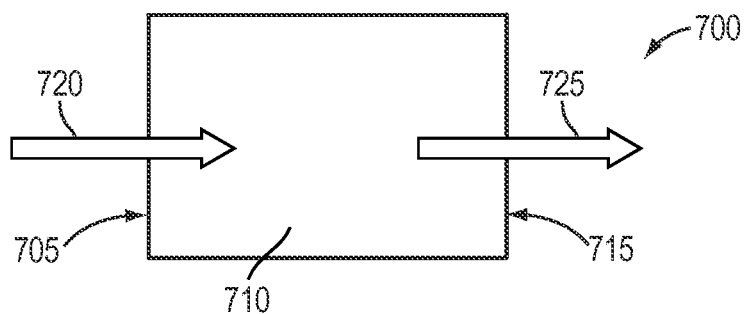
FIGS. 7 and 8 show fluorescent optics that can be used in conjunction with any of the flash lamps or apparatuses described herein.
Figure 8:
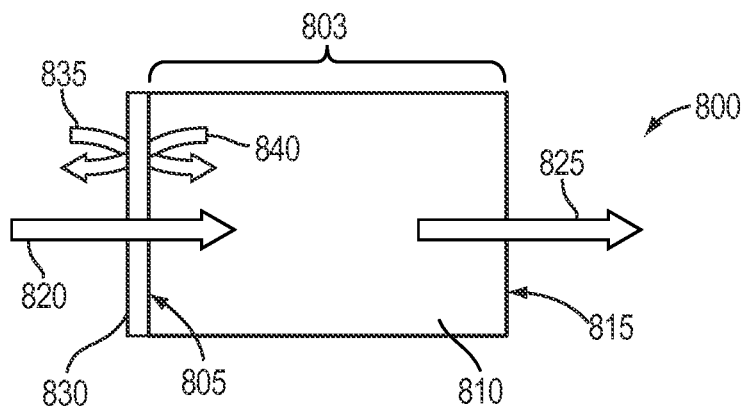

FIGS. 7 and 8 show fluorescent optics that can be used in conjunction with any of the flash lamps or apparatuses described herein.

FIG. 7 shows an exemplary optic 700 having a first end 705, a fluorescent material 710, and a second end 715. The first end 705 is adapted to transmit a first band 720 of electromagnetic radiation (i.e., electromagnetic radiation emitted from a flash lamp) to the fluorescent material 710. The fluorescent material 710 is adapted to absorb (e.g., absorb at least a portion of) the first band 720 of electromagnetic radiation and emit a second band 725 of electromagnetic radiation. In various embodiments, the fluorescent material 710 substantially absorbs (e.g., greater than about 80%, greater than about 90%, or about 100% of) the first band 720 of electromagnetic radiation. The second end 715 is adapted to be positioned relative to the organic tissue and deliver the second band 725 of electromagnetic radiation to treat the organic tissue. For example, the second end 715 can be positioned adjacent to, contacting, or touching the organic tissue either directly or though an index matching element (e.g., a non-light guide, non-filtering liquid or gel). However, a light guide is not necessary to couple the second band 725 into the organic tissue. In this, and other exemplary embodiments, band can refer to a single wavelength (e.g., when used in conjunction with a coherent light source) or multiple wavelengths within a range (e.g., when used in conjunction with an incoherent light source). In one embodiment, the optic 700 also includes a second band reflector (not shown) disposed relative to at least one surface of the optic. The second band reflector can reflect at least a portion of the second band of radiation, to direct the portion towards the organic tissue.

In various embodiments, the fluorescent material 710 includes a fluorescent crystal, glass, polymer, liquid, or dye. In general, the fluorescent substance is capable of modulating (e.g., transforming, converting, or varying) at least one property of the electromagnetic radiation. For example, the fluorescent substance can be a fluorescent crystal, glass, polymer, liquid, or dye selected to convert the electromagnetic radiation from at least one first wavelength to at least one second wavelength. In some embodiment, more than one fluorescent material 710 can be employed. Accordingly, at least one fluorescent material 710 can be selected depending upon the desired treatment and/or desired emission wavelength. Because the emission wavelength can be controlled by selecting one or more appropriate fluorescent material 710, the optic 700 does not require a filter to obtain a desired emission wavelength. The absorbing and emitting wavelengths of the fluorescent material 710 can be selected by the user or a technician. Since the optic 700 is in contact with or adjacent to the biologic tissue, no light guiding means between the body and the tissue need be used.

In various embodiments, the fluorescent material 710 is a fluorescent crystal, glass, or polymer. For example the fluorescent material 710 can include at least one of a Ti-sapphire, ruby, and alexandrite. The fluorescent material 710 can include a fluorescent glass such as LUMILASS-R7/G9/B manufactured by Sumita Optical Glass, Inc. The fluorescent material 710 can include a fluorescent polymer such as poly (methyl methacrylate) (PMMA) or polyurethane, which can include a fluorescent dye. The fluorescent material 710 can include a laser crystal such as a Nd:YAG crystal, or an erbium glass or crystal, or a uranium glass or crystal.

In various embodiments, the fluorescent material 710 can change blue-green light to yellow and/or red light. For example, the fluorescent material 710 can be a liquid dye such as pyrromethene, preferably pyrromethene 580, for changing light emitted from a source to a desired wavelength. A suitable concentration can be a concentration sufficient to achieve greater than about 80%, greater than about 90%, or about 100% absorption of electromagnetic radiation. The liquid base can be, for example, an alcohol or a mixture of alcohols, preferably methanol and/or ethanol. In various embodiments, the fluorescent substance can include 4-dicyanomethylene-2-methyl-6-(p(dimethylamino)styryl)-4H-pyran (DCM), pyrromethene, fluorescein, coumarin, stilbene, umbelliferone, tetracene, malachite green, rhodamin, or rhodamin 6G. In various embodiments, adamantane can be added to a fluorescent substance to prolong its life. In some embodiments, cycloheptatriene and cyclooctatetraene can be added to a fluorescent substance as triplet quencher, to increase output power. In certain embodiments, a fluorescent substance can include one or more pyrromethanes.

In various embodiments, harmful, non-therapeutic, or otherwise undesirable wavelength(s) of electromagnetic radiation do not pass through (e.g., no substantial or meaningful amount passes through) the optic and reach the organic tissue. The optic can be at least partially non-transparent to certain electromagnetic radiation emitted from a source of electromagnetic radiation (not shown), to prevent that certain wavelength(s) from reaching the organic tissue. Non-transparency (e.g., prevention of transmission by reflection or absorption) can be partial or complete, and can pertain to non-transparency to electromagnetic radiation having a particular spectrum, intensity, or both. The optic and source of electromagnetic radiation can be selected such that the fluorescent material 710 substantially absorb the electromagnetic radiation emitted from the source (e.g., the first band 720) and substantially converts that electromagnetic radiation into the second band 725 of electromagnetic radiation. For example, a Ti-sapphire (i.e., a fluorescent material) can substantially absorb the electromagnetic radiation emitted from a Nd:YAG laser operating at 532 m (i.e., a first band of electromagnetic radiation, the absorption range is about 400 to about 600 nm) and substantially emit electromagnetic radiation at about 795 nm (i.e., the second band of electromagnetic radiation, the emission range is about 660 to about 1050 nm) for treating organic tissue.

FIG. 8 shows an exemplary apparatus 800 for treating organic tissue including an optic 803 and a filter 830. The optic 803 has a first end 805, a second end 815, and a fluorescent material 810. The fluorescent material 810 is adapted to substantially absorb a first band 820 of electromagnetic radiation (i.e., electromagnetic radiation emitted from a flash lamp) and emit a second band 825 of electromagnetic radiation. The second end of the optic 815 is for contacting organic tissue (not shown) and delivering the second band 825 of electromagnetic radiation to treat the organic tissue. The optic 803, first end 805, fluorescent material 810, second end 815, first band 820 of electromagnetic radiation, and second band 825 of electromagnetic radiation can include any one or more of the features of respective elements optic 700, first end 705, fluorescent material 710, second end 715, first band 720 of electromagnetic radiation, and second band 725 of electromagnetic radiation discussed in connection with FIG. 7.

The filter 830 is disposed relative to the first end 805 of the optic and is adapted to substantially transmit the first band 820 of electromagnetic radiation to the fluorescent material 810 and to block (e.g., reflect, absorb, or both) other electromagnetic radiation 835. Although the filter 830 is illustrated in contact with the first end 805, the filter can be positioned anywhere between the source of electromagnetic radiation and the first end 805. In various embodiments, the filter 830 can block a portion 840 of the second band 825 of electromagnetic radiation, to direct the portion 840 towards the organic tissue. In some embodiments, the filter 830 is embodied by an element functioning as a mirror (e.g., reflecting an undesired wavelength) or partial mirror. In certain embodiments, the filter 830 is embodied by an element functioning as an absorbing filter (e.g., absorbing an undesired wavelength). The filter 830 can also function as both a mirror and an absorbing filter. Blocking other electromagnetic radiation 835 and blocking a portion 840 of the second band 825 are separable functions (e.g., a filter 830 can have any one or both functions).

In various embodiments, a filter 830 can be a dichroic element, for example, a dichroic filter, thin-film filter, dichroic mirror, or dichroic reflector. A filter 830 can include one or more metal oxide layers. Examples of a filter 830 include the model number FF01-6804/SP filter available from SEMROCK®, Inc., as well as the BRIGHTLINE® filters also available from SEMROCK®, Inc. In one embodiment, the filter 830 reflects wavelengths greater than about 600 nm and less than about 440 nm.

The filter can be a coating on a surface of the first end of the optic. In some embodiments, the filter can be a coating on all surfaces of the optic except the second end of the optic.

Application No. 60/953,611, filed Aug. 2, 2007 and entitled "Device and method for treatment of organic tissue" by Gustavsson and to application Ser. No. 12/184,821, filed Aug. 1, 2008 and entitled "Device and Method for Treatment of Organic Tissue" by Gustavsson, the disclosures of which are incorporated herein by reference in their entirety, disclose fluorescent optics that can be used in conjunction with any of the flash lamps or apparatuses described herein.

Figure 9:
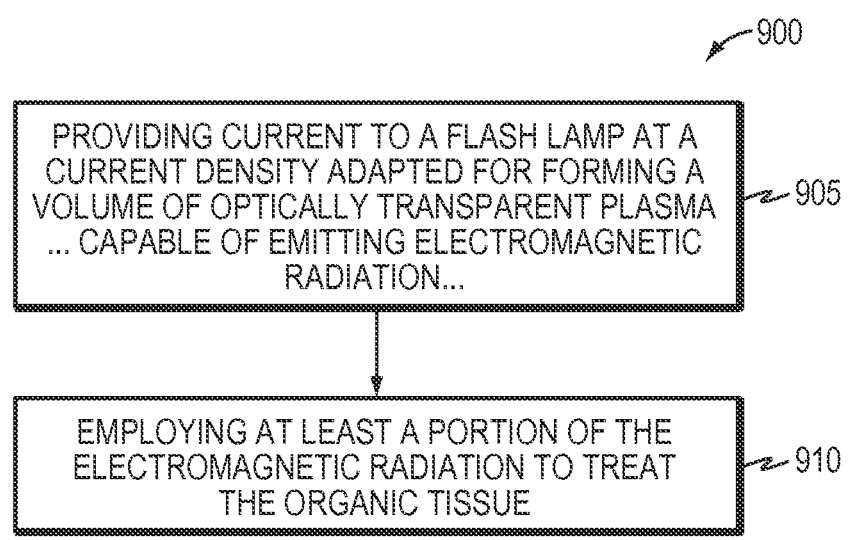
FIG. 9 shows a method for treating organic tissue.

FIG. 9 shows a method 900 for treating organic tissue. The method 900 includes step 905 of providing current to a flash lamp at a current density adapted for forming a volume of optically transparent plasma within a bore of the flash lamp. In step 905, the volume of optically transparent plasma is capable of emitting electromagnetic radiation and allowing the transmission of the electromagnetic radiation through the volume of optically transparent plasma. The method 900 includes step 910 of employing at least a portion of the electromagnetic radiation to treat the organic tissue. The portion of the electromagnetic radiation can include electromagnetic radiation emitted from throughout the volume of optically transparent plasma and transmitted from within the volume of optically transparent plasma and through the volume of optically transparent plasma.

In various embodiments, the method 900 also includes reflecting a second portion of the electromagnetic radiation back through the optically transparent plasma to the delivery system, to increase the portion of the emitted electromagnetic radiation to treat the organic tissue. Reflecting a second portion of the electromagnetic radiation back through the optically transparent plasma, which is described in connection with FIG. 6 can be advantageous because it can increase the operating efficiency of the apparatus.

In various embodiments, step 910 of employing at least a portion of the electromagnetic radiation to treat the organic tissue can include delivering the portion of the electromagnetic radiation to the organic tissue. In one embodiment, the portion of the electromagnetic radiation can travel directly from a naked lamp to the organic tissue. In one embodiment, the portion of the electromagnetic radiation can travel through a waveguide of light pipe to the organic tissue. A filter can be used between the flash lamp and the organic tissue, to prevent harmful or otherwise undesirable wavelengths from reaching the organic tissue.

In various embodiments, step 910 of employing at least a portion of the electromagnetic radiation to treat the organic tissue can include (i) transforming the portion of the electromagnetic radiation into radiation having a second wavelength and (ii) delivering the radiation having the second wavelength to the organic tissue. Transforming the portion of the electromagnetic radiation can be achieved by use of a fluorescent optic, such as the optics described in connection with FIGS. 7 and 8. Transforming the portion of the electromagnetic radiation can be achieved by use of a laser dye, where the flash lamp is used to pump the laser dye.

In various embodiments, delivery of electromagnetic radiation to the orgzanic tissue can be terminated upon reaching a treatment endpoint (e.g., vessel graying, reduction or termination of blood refill post external pressure, pigment darkening, transient degrees of erythema, partial or general oedemas, perifollicular oedema).

EXAMPLE 1

TABLE 1.1 lists parameters for an exemplary flash lamp apparatus.

| Lamp Parameters: | | Individual Pulses (within Pulse Train): | | Pulse Train Geometry: | |
|---|---|---|---|---|---|
| Arc Length: | 6 cm | Pulse Width: | 3 ms | Pulses: | 7 per train |
| Bore: | 13 mm | Bank Voltage: | 200 V/lamp | Duty Cycle: | 60.0% |
| Gas Type: | Xe | Simmer Current: | 1000 mA | Frequency (of Train): | 1 Hz |
| Pressure: | 450 Torr | Total Capacitans: | 0.15 F | | |
| Lamp Material: | Clear Fused Quartz | | | | |

TABLE 1.2 list conditions for a flash lamp operated under the parameters listed in Table 1.1.

| Lamp Conditions: | | Pulse Train Conditions: | |
|---|---|---|---|
| $K_0$ (Lamp Impedance): | 5.91 | Pulse width: | 0.033 s |
| Average Power: | 2067 W | Energy/Train: | 2067 J |
| Peak Power: | 229000 W | Explosion Energy: | 17016 J |
| Peak Current: | 1145 Amps | E/Explosion Energy: | 12.1% |
| RMS Current: | 44 Amps | | |
| C/Pulse: | 3.44 C | | |
| Current Density: | 863 Amp/cm$^2$ | | |
| Energy/Pulse: | 687 J | | |
| E/Explosion Energy: | 13.4% | | |
| Wall Loading: | 84 W/cm$^2$ | | |

Operating the flash lamp apparatus described in Tables 1.1 and 1.2 with a long pass filter cutting at 535 nm can emit 888 J of electromagnetic radiation, which corresponds to an overall electro-optical efficiency of 43% (i.e., Eout/(E/Train) =888/2067=43%). If, for example, a 535 nm filter is added to the apparatus (e.g., for treating vascular lesions), operating the flash lamp apparatus to produce a 12 cm$^2$ spot size can produce a fluence of about 74 J/cm$^2$ (e.g., substantially more than the 30 j/cm$^2$ needed for a vascular lesion treatment). If, for example, a 615 nm filter is added to the apparatus (e.g., for a hair removal treatment), operating the flash lamp apparatus to produce a 12 cm² spot size can produce a fluence of about 60 J/cm² (e.g., substantially more then the 41 J/cm² needed for a hair removal treatment).

EXAMPLE 2

TABLE 2.1 lists parameters for an exemplary flash lamp apparatus.

| Lamp Parameters: | | Individual Pulses (within Pulse Train): | | Pulse Train Geometry: | |
|---|---|---|---|---|---|
| Arc Length: | 6 cm | Pulse Width: | 3 ms | Pulses: | 7 per train |
| Bore: | 13 mm | Bank Voltage: | 170 V/lamp | Duty Cycle: | 50.0% |
| Gas Type: | Xe | Simmer Current: | 1000 mA | Frequency (of Train): | 1 Hz |
| Pressure: | 450 Torr | Total Capacitans: | 0.15 F | | |
| Lamp Material: | Clear Fused Quartz | | | | |

TABLE 2.2 list conditions for a flash lamp operated under the parameters listed in Table 2.1.

| Lamp Conditions: | | Pulse Train Conditions: | |
|---|---|---|---|
| $K_0$ (Lamp Impedance): | 5.91 | Pulse width: | 0.033 s |
| Average Power: | 1394 W | Energy/Train: | 1394 J |
| Peak Power: | 140590 W | Explosion Energy: | 18498 J |
| Peak Current: | 827 Amps | E/Explosion Energy: | 7.5% |
| RMS Current: | 32 Amps | | |
| C/Pulse: | 2.48 C | | |
| Current Density: | 623 Amp/cm² | | |
| Energy/Pulse: | 422 J | | |
| E/Explosion Energy: | 8.2% | | |
| Wall Loading: | 57 W/cm² | | |

Operating the flash lamp apparatus described in Tables 2.1 and 2.2 with a long pass filter cutting at 535 nm can emit 600 J of electromagnetic radiation, which corresponds to an overall electro-optical efficiency of 43% (i.e., Eout/(E/Train) =600/1394=43%). If, for example, a 535 nm filter is added to the apparatus (e.g., for treating vascular lesions), operating the flash lamp apparatus to produce a 12 cm² spot size can produce a fluence of about 50 J/cm² (e.g., substantially more than the 30 J/cm² needed for a vascular lesion treatment). If, for example, a 615 nm filter is added to the apparatus (e.g., for a hair removal treatment), operating the flash lamp apparatus to produce a 12 cm² spot size can produce a fluence of about 41 J/cm² (e.g., about the 41 J/cm² needed for a hair removal treatment).

While the invention has been particularly shown and described with reference to specific embodiments, it should be understood by those skilled in the art that various changes in form and detail may be made without departing from the spirit and scope of the invention as defined by the appended claims.

What is claimed is:

1. An apparatus configured for treating organic tissue, comprising:
    a flash lamp defining a bore, the flash lamp configured to form a volume of optically transparent plasma within the bore;
    a current source configured to deliver current to the flash lamp and operate the flash lamp at a current density that facilities the formation of the volume of optically transparent plasma within the bore, the current density being less than 1,000 A/cm²,
    wherein the volume of optically transparent plasma is configured to emit electromagnetic radiation from within the plasma to outside of the plasma and allow the transmission of the electromagnetic radiation through the volume of optically transparent plasma,
    wherein the optically transparent plasma has a transmission coefficient of greater than 0.35 for a 1 cm path length at a wavelength of 5,500 Å; and
    a delivery system configured to receive at least a portion of the electromagnetic radiation and to direct said portion of electromagnetic radiation to organic tissue.

2. The apparatus of claim 1, further comprising a reflector disposed relative to the flash lamp and configured to reflect a second portion of the electromagnetic radiation back through the optically transparent plasma to the delivery system.

3. The apparatus of claim 1, wherein the portion of the electromagnetic radiation comprises electromagnetic radiation emitted from within the volume of optically transparent plasma and transmitted from within the volume of optically transparent plasma and through the volume of optically transparent plasma.

4. The apparatus of claim 1, wherein the delivery system comprises a waveguide configured to receive the portion of electromagnetic radiation from the flash lamp and further configured to deliver the portion of the electromagnetic radiation to the organic tissue.

5. The apparatus of claim 1, wherein the delivery system comprises a body configured to receive electromagnetic radiation from the flash lamp and at least partially transforming the electromagnetic radiation into radiation having a second wavelength.

6. The apparatus of claim 1, wherein the bore diameter is greater than 7 mm.

7. The apparatus of claim 1, wherein the bore diameter is greater than 9 mm.

8. The apparatus of claim 1, wherein the bore diameter is greater than 11 mm.

9. The apparatus of claim 1, wherein the flash lamp comprises a cathode and an anode separated by an arc path length, and an arc path length to bore diameter ratio of less than 1.

10. The apparatus of claim 1, wherein the flash lamp comprises a cathode and an anode separated by an arc path length, and an arc path length to bore diameter ratio of less than 6.

11. The apparatus of claim 1, wherein the flash lamp comprises a cathode and an anode separated by an arc path length, and an arc path length to bore diameter ratio of less than 12.

* * * * *

UNITED STATES PATENT AND TRADEMARK OFFICE
CERTIFICATE OF CORRECTION

PATENT NO. : 8,858,229 B2  
APPLICATION NO. : 12/199488  
DATED : October 14, 2014  
INVENTOR(S) : Morgan Lars Ake Gustavsson Page 1 of 1

It is certified that error appears in the above-identified patent and that said Letters Patent is hereby corrected as shown below:

Specification

In column 6 at line 49, Change "1," to --11,--.

In column 12 at line 32, Change "532 m" to --532 nm--.

In column 14 at line 65, Change "30 j/cm2" to --30 J/cm2--.

Claims

In column 16 at lines 41-42, In Claim 5, change "transforming" to --transform--.

Signed and Sealed this  
Tenth Day of November, 2015

Michelle K. Lee  
*Director of the United States Patent and Trademark Office*